US011135098B2

(12) United States Patent
Yamada

(10) Patent No.: US 11,135,098 B2
(45) Date of Patent: Oct. 5, 2021

(54) MULTI-PLY SHEET PRODUCTION METHOD AND MULTI-PLY SHEET PRODUCTION DEVICE

(71) Applicant: Kikuo Yamada, Shinagawa-ku (JP)

(72) Inventor: Kikuo Yamada, Shinagawa-ku (JP)

(*) Notice: Subject to any disclaimer, the term of this patent is extended or adjusted under 35 U.S.C. 154(b) by 1 day.

(21) Appl. No.: 16/084,388

(22) PCT Filed: Mar. 8, 2017

(86) PCT No.: PCT/JP2017/009262
§ 371 (c)(1),
(2) Date: Sep. 12, 2018

(87) PCT Pub. No.: WO2017/159498
PCT Pub. Date: Sep. 21, 2017

(65) Prior Publication Data
US 2019/0076302 A1 Mar. 14, 2019

Related U.S. Application Data

(60) Provisional application No. 62/308,974, filed on Mar. 16, 2016.

(51) Int. Cl.
*A61F 13/15* (2006.01)
*B32B 5/04* (2006.01)
(Continued)

(52) U.S. Cl.
CPC ........ *A61F 13/15699* (2013.01); *A61F 13/15* (2013.01); *A61F 13/49* (2013.01);
(Continued)

(58) Field of Classification Search
CPC ............ A61F 2013/51452; A61F 13/15; A61F 13/49; A61F 13/51; A61F 13/49019;
(Continued)

(56) References Cited

U.S. PATENT DOCUMENTS

2004/0121683 A1* 6/2004 Jordan ..................... B32B 5/26
442/182
2006/0142728 A1 6/2006 Tabor et al.
(Continued)

FOREIGN PATENT DOCUMENTS

EP 2 767 267 A1 8/2014
JP 61-289163 A 12/1986
(Continued)

OTHER PUBLICATIONS

International Search Report dated Jun. 13, 2017, in PCT/JP2017/009262 filed Mar. 8, 2017.
(Continued)

*Primary Examiner* — Vishal I Patel
(74) *Attorney, Agent, or Firm* — Oblon, McClelland, Maier & Neustadt, L.L.P.

(57) ABSTRACT

Provided is a multi-ply sheet production method and a multi-ply sheet production device for producing a multi-ply sheet which uses an elastic member, exhibits stretchability, and has reduced residual strain. The multi-ply sheet production method includes forming a multi-ply sheet by joining a first fibrous sheet, and a second fibrous sheet including a material containing a cellulose-based component, with an elastic member interposed therebetween, the elastic member being in a stretched state and coated with an adhesive on peripheral surface, and then heat-treating the multi-ply sheet at a temperature in accordance with the thermal characteristics of the adhesive.

4 Claims, 11 Drawing Sheets

(51) Int. Cl.
    *B32B 5/26* (2006.01)
    *B32B 37/12* (2006.01)
    *A61F 13/51* (2006.01)
    *A61F 13/49* (2006.01)
    *B32B 37/14* (2006.01)
    *D21H 27/34* (2006.01)
    *D21H 27/32* (2006.01)
    *A61F 13/496* (2006.01)
    *A61F 13/514* (2006.01)
    *B32B 37/20* (2006.01)

(52) U.S. Cl.
    CPC ........ *A61F 13/4902* (2013.01); *A61F 13/496* (2013.01); *A61F 13/49019* (2013.01); *A61F 13/51* (2013.01); *A61F 13/51401* (2013.01); *B32B 5/04* (2013.01); *B32B 5/26* (2013.01); *B32B 37/12* (2013.01); *B32B 37/14* (2013.01); *D21H 27/32* (2013.01); *D21H 27/34* (2013.01); *A61F 2013/15902* (2013.01); *A61F 2013/49025* (2013.01); *A61F 2013/49033* (2013.01); *A61F 2013/51452* (2013.01); *B32B 37/1207* (2013.01); *B32B 37/20* (2013.01); *B32B 2555/02* (2013.01)

(58) Field of Classification Search
    CPC ............ A61F 13/15699; A61F 13/4902; A61F 13/51401; A61F 2013/49033; A61F 2013/15902; A61F 2013/49025; A61F 13/496; D21H 27/32; D21H 27/34; B32B 5/26; B32B 5/04; B32B 37/14; B32B 37/20; B32B 37/1207; B32B 2555/02; B32B 37/12
    See application file for complete search history.

(56) References Cited

U.S. PATENT DOCUMENTS

| | | |
|---|---|---|
| 2006/0148358 A1* | 7/2006 | Hall .......................... B32B 5/08 442/328 |
| 2013/0306226 A1 | 11/2013 | Zink et al. |
| 2013/0310796 A1 | 11/2013 | Zink et al. |
| 2013/0310797 A1 | 11/2013 | Zink et al. |
| 2013/0324956 A1 | 12/2013 | Zink et al. |
| 2014/0005020 A1 | 1/2014 | Lavon et al. |
| 2014/0234586 A1* | 8/2014 | Chen ...................... B32B 27/12 428/188 |
| 2014/0302286 A1 | 10/2014 | Okuda et al. |
| 2015/0328056 A1 | 11/2015 | Een et al. |
| 2016/0220425 A1 | 8/2016 | Zink et al. |
| 2016/0220426 A1 | 8/2016 | Zink et al. |
| 2016/0235599 A1 | 8/2016 | Zink et al. |
| 2018/0092785 A1 | 4/2018 | Zink et al. |

FOREIGN PATENT DOCUMENTS

| | | |
|---|---|---|
| JP | 2008-525104 A | 7/2008 |
| JP | 2015-92954 A | 5/2015 |
| JP | 2016-506322 A | 3/2016 |
| WO | WO 2013/173310 A1 | 11/2013 |
| WO | WO 2014/005045 A1 | 1/2014 |

OTHER PUBLICATIONS

Extended European Search Report dated Jul. 4, 2019 in European Patent Application No. 17766499.2, 8 pages.

* cited by examiner

MULTI-PLY SHEET PRODUCTION METHOD AND MULTI-PLY SHEET PRODUCTION DEVICE

TECHNICAL FIELD

The present invention relates to a multi-ply sheet production method and a multi-ply sheet production device.

BACKGROUND ART

Technology for reducing the residual strain of multi-ply sheets, which are stretchable and are obtained by laminating fibrous sheets, is known in the related art (for example, see PTL 1).

As an adhesive for joining spunlaced nonwoven fabrics and spunbonded nonwoven fabrics themselves, PTL 1 discloses an elastic stretchable hot-melt adhesive which has a residual strain per stretch amount of 15% or less when stretched 50% and followed by an immediate release of the stretched state.

Meanwhile, a multi-ply sheet having stretchability using an elastic member is also known (see PLT 2 for example).

Patent document 2 discloses that a back sheet and an external sheet are joined to each other, and a plurality of elastic members in a stretched state are joined to both the outer surface of the back sheet and the inner surface of the external sheet.

CITATION LIST

Patent Literature

PTL 1: JP 10-286279 A
PTL 2: JP 2016-96882 A

SUMMARY OF INVENTION

Technical Problem

However, even when the method disclosed by PTL 1 is simply applied to a multi-ply sheet like that disclosed by PTL 2, it is difficult to reduce the residual strain in this type of multi-ply sheet.

Therefore, an object of the present invention is to provide a multi-ply sheet production method and a multi-ply sheet production device for producing a multi-ply sheet which uses an elastic member, exhibits stretchability, and has reduced residual strain.

Solution to Problem

The multi-ply sheet production method according to a first aspect of the present invention includes forming a multi-ply sheet by joining a first fibrous sheet, and a second fibrous sheet made from a material containing a cellulose-based component, with an elastic member interposed therebetween, the elastic member being in a stretched state and coated with an adhesive on a peripheral surface; and then heat-treating the multi-ply sheet at a temperature in accordance with the thermal characteristics of the adhesive.

The multi-ply sheet production device according to a second aspect of the present invention includes an adhesive coating device configured to coat an elastic member with an adhesive; a pressing device configured to sandwich the elastic member with the adhesive between a first fibrous sheet, and a second fibrous sheet made from a material containing a cellulose-based component, and press to form a multi-ply sheet; and a heating device configured to heat-treat the multi-ply sheet at a temperature in accordance with the thermal characteristics of the adhesive.

Advantageous Effect of Invention

According to the present invention, a multi-ply sheet which uses an elastic member, exhibits stretchability, and has reduced residual strain can be produced.

DESCRIPTION OF EMBODIMENT

Embodiments of the present invention are described below with reference to the drawings.

First Embodiment

In the present embodiment, a case in which a base fabric 1, which is a multi-ply sheet, is primarily used as a surface material 15 of an absorbent body 14 (see, FIGS. 6 and 7) is described. Examples of liquids that are absorbed by the absorbent body 14 include urine, sweat, blood, lymphatic fluids, and other such body fluids, and in the description below, the present invention is described with the assumption primarily of urine.

Figure 1:
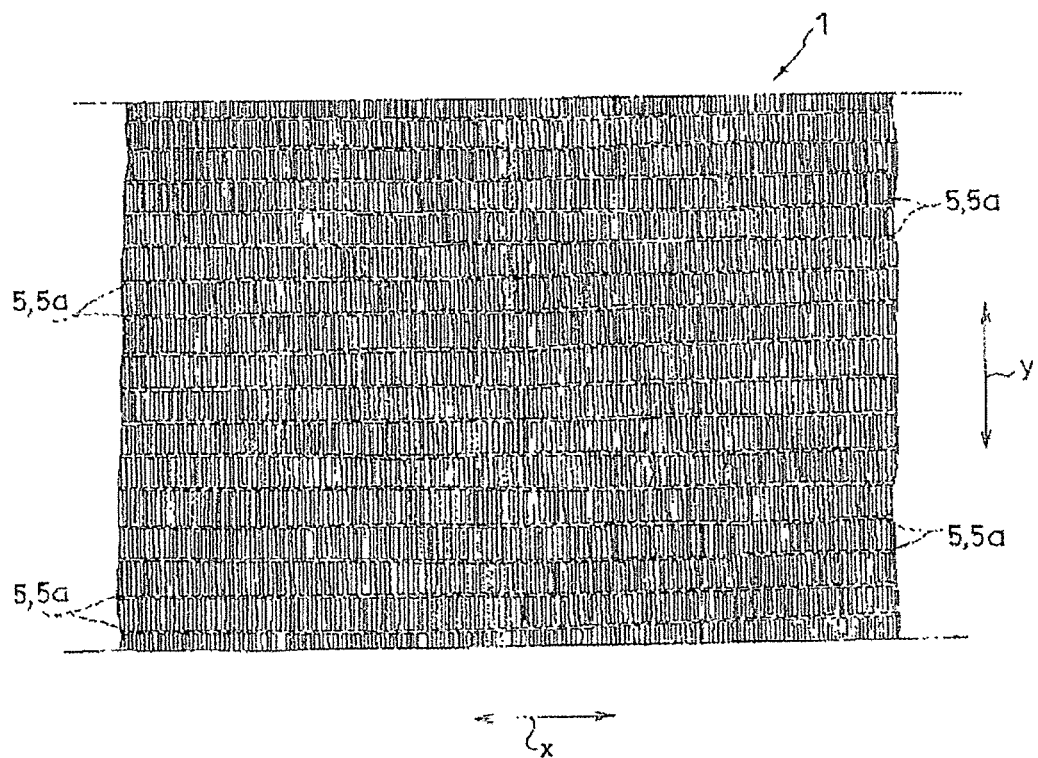
FIG. 1 is a drawing illustrating a base fabric according to one embodiment of the present invention.
Figure 2:
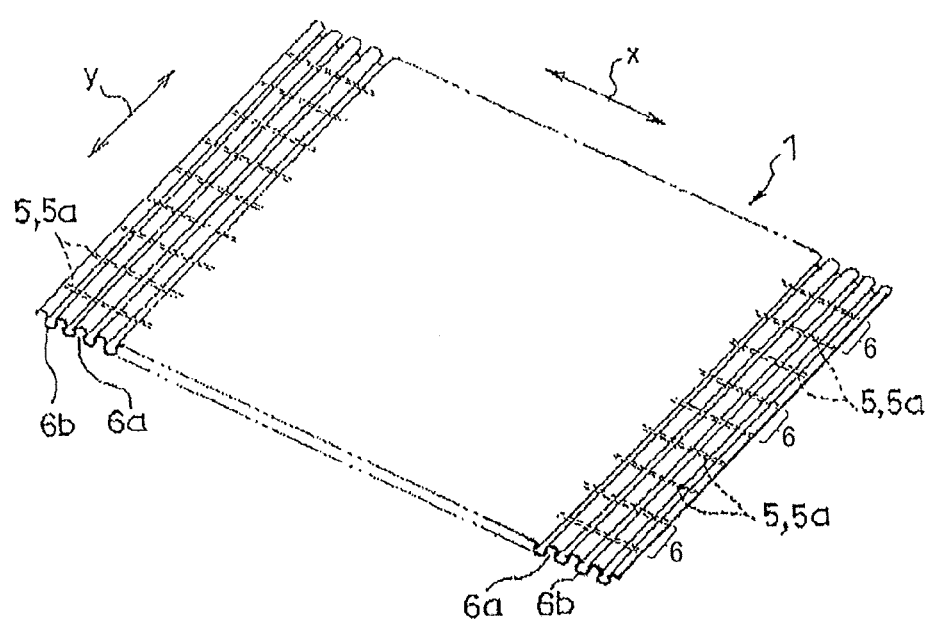
FIG. 2 is a perspective view of the base fabric illustrated in FIG. 1.
Figure 3:
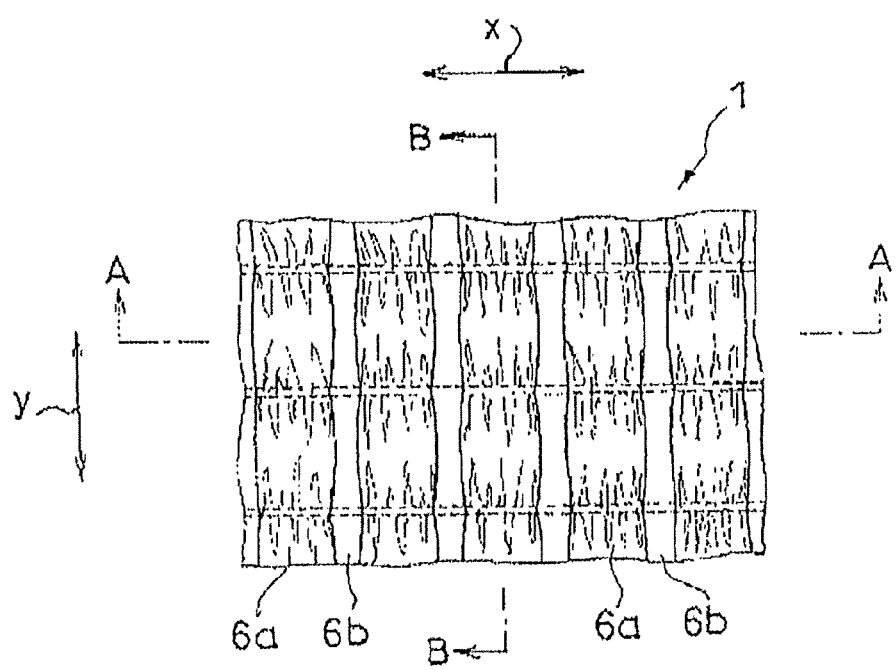
FIG. 3 is an enlarged view of the base fabric illustrated in FIG. 1.

FIG. 1 is a drawing illustrating a base fabric 1 according to the first embodiment of the present invention, FIG. 2 is a perspective view of the base fabric 1 illustrated in FIG. 1, and FIG. 3 is an enlarged view of the base fabric 1 illustrated in FIG. 1. The base fabric 1 is described below with reference to FIGS. 1 to 3.

In FIG. 1, the base fabric 1 has a long configuration that is continuous in the x-direction, which is the longitudinal direction (first direction).

As is clear from FIGS. 1 and 2, the elastic member 5 is provided within the base fabric 1 along the x-direction, and a plurality of elastic members 5 is provided at prescribed intervals in the y-direction, which is the short direction (second direction) of the base fabric 1. The elastic members 5 expand and contract along the x-direction. As illustrated in FIG. 2, an uneven surface, that is, shirring portions are formed in the base fabric 1 by the plurality of elastic members 5.

As the elastic member 5, a stretchable linear elastic body 5a is used, and urethane, silicone, butadiene, or a styrene-butadiene based synthetic rubber, or natural rubber can be used.

Note that in a case where a lattice-shaped elastic member is used, the above-mentioned shirring portion can be formed with one lattice shape. Moreover, a stretchable film may also be used in place of the plurality of elastic members 5. As the stretchable film, a urethane film, silicone film, elastomer film, or the like can be used.

In the below description, polyurethane is used as the linear elastic body 5a.

Figure 4:
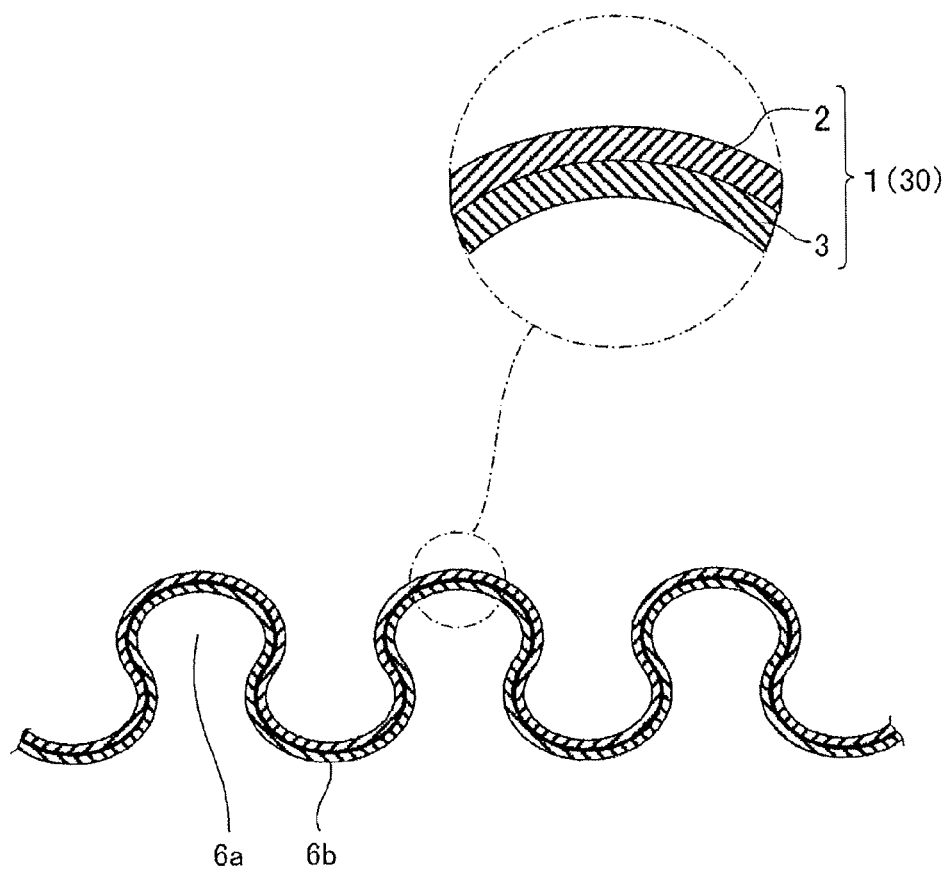
FIG. 4 is a cross-sectional view along a line A-A in FIG. 3.
Figure 5:
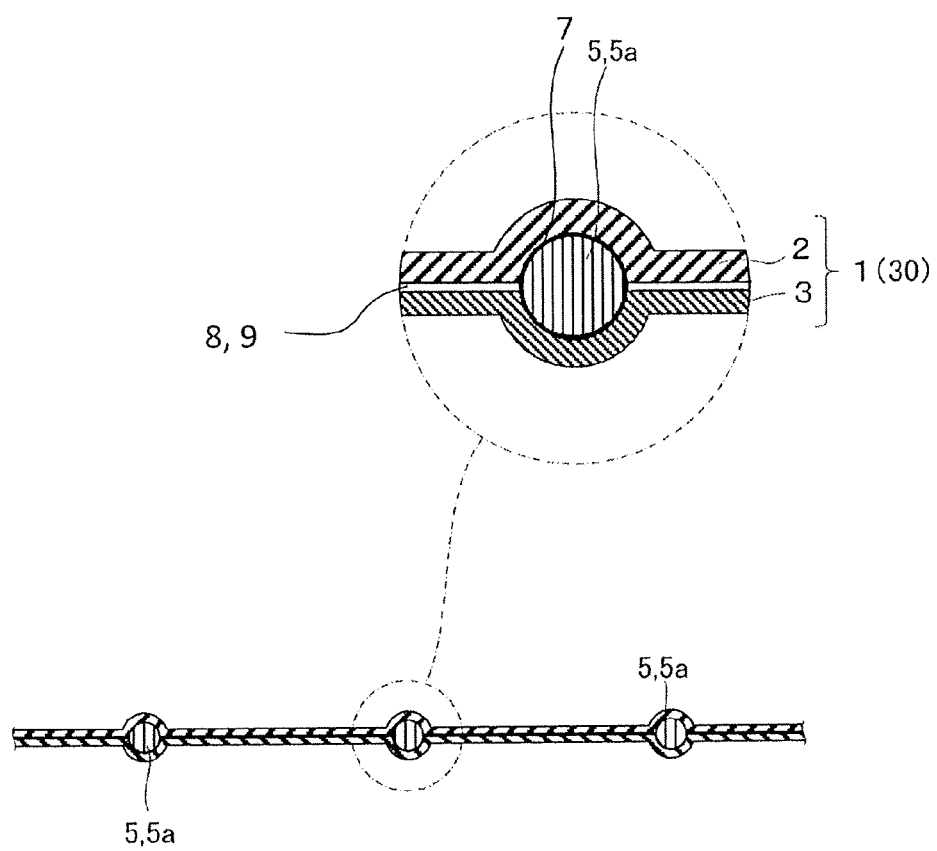
FIG. 5 is a cross-sectional view along a line B-B in FIG. 3.

FIG. 4 is a cross-sectional view along a line A-A in FIG. 3, and FIG. 5 is a cross-sectional view along a line B-B in FIG. 3. As illustrated in FIGS. 4 and 5, the base fabric 1 is a multi-ply sheet 30 obtained by laminating a first fibrous sheet 2 and a second fibrous sheet 3, the first fibrous sheet 2 having air permeability, and the second fibrous sheet 3 being liquid diffusible. The first fibrous sheet 2 is formed of a fiber layer having air permeability, and the second fibrous sheet 3 is formed of a liquid diffusible fiber layer. The multi-ply sheet 30 is configured with two layers in this manner.

Note that in the present embodiment, as will be described below, in a case where the base fabric 1 is adapted as the surface material 15, the first fibrous sheet 2 becomes the skin surface side of a user wearing the absorbent body 14, and the second fibrous sheet 3 becomes the non-skin surface side that does not contact the skin of the user. Moreover, the base fabric 1 is adapted to the surface material 15 such that the x-direction of the base fabric 1 in FIG. 1 matches the X-direction in FIG. 6, and the y-direction in FIG. 1 matches the Y-direction in FIG. 6.

The first fibrous sheet 2 is a nonwoven fabric, and a two-layer or a three-layer spunbonded nonwoven fabric can be used. In the present embodiment, the base fabric 1 is used as the surface material 15 of the absorbent body 14, and therefore use of a hydrophilic nonwoven fabric is preferable. In a case where hydrophilicity is required of the base fabric 1, a hydrophilization treatment such as the addition of a hydrophilizing agent to the base fabric 1 may be performed, for example.

Note that the basis weight of the first fibrous sheet 2 is, as one example, preferably 10 to 50 g/m², and is more preferably 10 to 20 g/m² from the viewpoint of production costs, but the basis weight is not limited thereto.

As the second fibrous sheet 3, paper such as toilet paper or crepe paper can be used, and pulp paper or a material having pulp as a main raw material, or in other words, a material containing a cellulose-based component can be used. Wood pulp, synthetic pulp, waste paper pulp, and the like can be used as the raw material pulp. Additionally, the material containing a cellulose-based component is not limited to natural fiber such as pulp, and regenerated fiber such as rayon can be used. Note that the basis weight of the second fibrous sheet 3 is, as one example, preferably 10 to 50 g/m². Moreover, in a case where paper is used, the second fibrous sheet 3 is preferably subjected to embossing, for example, to impart flexibility.

As illustrated in FIG. 5, in the present embodiment, the first fibrous sheet 2 and the second fibrous sheet 3 are joined by an adhesive 7 that is applied onto a peripheral surface of the elastic member 5. Therefore, a non-adhesive portion 8 where the adhesive 7 is not present is formed between the first fibrous sheet 2 and the second fibrous sheet 3, and a space 9 is formed by this non-adhesive portion 8. In the present embodiment, the space 9 is formed by the non-adhesive portion 8, and therefore various functions such as moisture transpiration ability, heat dissipation ability, and moisture permeability can be improved in the base fabric 1.

Note that in place of adhering through the elastic member 5, or in addition to adhering through the elastic member 5, at least one surface of the first fibrous sheet 2 and the second fibrous sheet 3 may be partially (intermittently) coated with the adhesive 7, to join the first fibrous sheet 2 and the second fibrous sheet 3. In this case as well, joining of the first fibrous sheet 2 and the second fibrous sheet 3 is partial (intermittent), and therefore the space 9 can be formed between the first fibrous sheet 2 and the second fibrous sheet 3.

To partially (intermittently) apply the adhesive 7, methods of application in a spray shape, linear shape, spot shape, stripe shape, spiral shape, block shape, pattern shape, and the like can be used, and such methods can be used individually or a plurality of methods thereof can be combined and used.

Moreover, as the adhesive 7, a pressure-sensitive adhesive, curable adhesive, or other various types of adhesives can be used, and in the present embodiment, a hot-melt adhesive is used. Note that joining of the first fibrous sheet 2 and the second fibrous sheet 3 is not limited to joining by adhesion, and various types of joining methods such as ultrasonic bonding and heat sealing can be used or can be used in combination.

As illustrated in FIGS. 2, 3, and 4, shirring portions are formed in the entire base fabric 1 by continuously forming peak portions 6a and valley portions 6b between adjacent linear elastic bodies 5a.

Note that intervals at which the linear elastic bodies 5a are provided in the y-direction may be nearly uniform intervals, or, for example, at peripheral sections of the base fabric 1, the intervals may be short and the linear elastic bodies 5a may be densely arranged. Furthermore, the intervals may be made shorter moving from the central portion of the base fabric 1 towards the peripheral sections. In place of this, or in combination therewith, the elastic force of the linear elastic bodies 5a of the peripheral sections of the base fabric 1, and the elastic force of the linear elastic bodies 5a of the central portion may be made to differ, and thereby the elastic force of the linear elastic bodies 5a of the peripheral sections may be made stronger.

Note that in the present embodiment, the peripheral section is a region of around 5 to 30% from a positive side end part and a region of 5 to 30% from a negative side end part in the Y-direction of the below-described surface material 15 of FIG. 6, and the central portion is a region excluding the peripheral sections.

As described above, the linear elastic bodies 5a are provided between the first fibrous sheet 2 and the second fibrous sheet 3. A plurality of concave-convex rows 6 is formed in the y-direction of FIGS. 1 and 2. The number of the linear elastic bodies 5a per unit surface area can be set as appropriate, but when the number of the linear elastic bodies 5a is increased and the interval between the linear elastic bodies 5a is decreased, the peak portions 6a and the valley portions 6b in one concave-convex row 6 are formed in a uniform shape, and this shape can be maintained. This prevents the shape of the shirring portion from collapsing, and improves the flexibility, moisture transpiration ability, heat dissipation ability, and moisture permeability of the base fabric 1.

From this standpoint, the pitch interval between mutual peak portions 6a is preferably 2.00 mm to 7.00 mm. The pitch interval between mutual peak portions 6a is more preferably 3.00 mm to 6.25 mm.

By reducing the pitch interval between the peak portions 6a, it is possible to form fine shirring, and therefore the external appearance is improved. Further, since an area of contact with the skin per one shirring decreases, contact with the skin is improved, and since the surface area increases, the ability to absorb sweat, or the like, is enhanced. Meanwhile, by increasing the pitch interval between the peak portions 6a, the elastic force of the linear elastic body 5a can be suitably reduced, and production costs can be reduced.

Note that FIGS. 1 and 2 illustrate the peak portions 6a and the valley portions 6b such that they are formed continuously, but depending on the number and arrangement of the linear elastic bodies 5a, the peak portions 6a and the valley portions 6b may be non-continuous, and may be shifted in the x-direction. However, in a case where the peak portions 6a and the valley portions 6b are formed shifted in the x-direction, and for example, the base fabric 1 is used as the surface material 15, urine or the like does not easily advance in the y-direction of FIGS. 1 and 2 (Y-direction of FIG. 6), and thus such a configuration can contribute to preventing side leakage.

The dimension of the base fabric 1 (also referred to as "multi-ply sheet 30") is long, and therefore the multi-ply sheet 30 is cut to obtain a predetermined length in the longitudinal direction (x-direction in FIGS. 1 and 2) of the multi-ply sheet 30. With this cutting, the first fibrous sheet 2, the second fibrous sheet 3 and the elastic member 5 are cut. By cutting the elastic member 5, the tension force applied to the elastic member 5 in the stretched state is released, and the elastic member 5 is contracted by the restoring force. Through the contraction stress at this time, the base fabric 1 (multi-ply sheet 30) configured from the first fibrous sheet 2, the second fibrous sheet 3, and the like receives force in a direction in which the length is made shorter. Thus, a plurality of concave-convex rows 6 is formed in the base fabric 1 (multi-ply sheet 30), and as a result, shirring portions are formed. In this manner, the base fabric 1 having shirring portions is produced.

Under the effect of the restoring force of the elastic members 5, the base fabric 1 is in a contracted state, that is, a non-stretched state, a plurality of the shirring portions extending in a direction (y-direction) that is orthogonal to the longitudinal direction (x-direction) of the elastic member 5, which is in this non-stretched state, is formed, and rows of shirring portions are formed in a pattern on the multi-ply sheet 30.

An elastic force is imparted to the multi-ply sheet 30 by the elastic members 5 arranged inside the multi-ply sheet 30. Therefore, when the base fabric 1 constituted by the multi-ply sheet 30 is stretched in the x-direction in FIGS. 1 and 2, the elastic members 5 extend, and thereby the base fabric 1 is also extended and expanded.

Also, when this state is canceled, the elastic member 5 is contracted by the restoring force, and as a result, the base fabric 1 is also restored to the original state. Because the base fabric 1 is stretchable in this manner, in a case where the base fabric 1 is used as the surface material 15, the base fabric 1 excels in a fitting feel with respect to the body.

Moreover, the base fabric 1 has a large surface area because the dimension as the surface material 15 is determined based on the dimension contracted by the restoring force of the elastic member 5. Therefore, the absorbent body 14 can absorb more body fluids through the surface material 15. The surface area can be increased 1.5 times to around 5 times by selecting the elastic force of the elastic member 5. For example, provided that the dimension of the base fabric 1 necessary in the x-direction in the non-stretched state is 300 mm, a multi-ply sheet 30 that is 450 mm to 1500 mm in the stretched state (elongated state) is used.

Also, for example, for a case in which the base fabric 1 is used as the surface material 15, consider an example in which the dimension in the x-direction is set to 360 mm, and the dimension in the y-direction is set to 100 mm. When the ratio of contraction (contraction rate) by the restoring force of the elastic member 5 is set to ⅓, the dimension in the x-direction of the base fabric 1 needs to be 1080 mm, which is obtained by multiplying by the inverse number of the contraction rate of the elastic member 5, and the dimension in the y-direction needs to be 100 mm because the restoring force of the elastic member 5 does not act in the y-direction.

However, when the base fabric 1 is actually cut after the first fibrous sheet 2 and the second fibrous sheet 3 have been joined with the elastic member 5 interposed therebetween, in some cases the contraction rate becomes ½ for a contraction of about 540 mm. This is thought to be due to the influence of residual strain that is generated during the process of producing the surface material 15. The residual strain naturally decreases over time, but when a surface material 15 with the residual strain remaining is used in the absorbent body 14, the absorbent body 14 deforms.

Therefore, in the present embodiment, the residual strain is reduced from the surface material 15 by using a first heating device 19, a second heating device 20, and a third heating device 45 (see FIG. 9) to heat the elastic member 5 used in the surface material 15, and the cured adhesive 7. Thus, a surface material 15 that is close to the theoretical contraction rate of the elastic member 5 can be produced. Namely, in the above-mentioned example, a contraction rate of ⅓ can be nearly achieved with respect to the surface material 15. As a result, deformation of the absorbent body 14 provided with the surface material 15 can be prevented.

To examine the impact that the second fibrous sheet 3 has on the contraction of the multi-ply sheet 30, the following comparison was performed. A multi-ply sheet 30 obtained by laminating the first fibrous sheet 2 and the second fibrous sheet 3, and a multi-ply sheet that used the same nonwoven fabric as the first fibrous sheet 2 in place of the second fibrous sheet 3 (multi-ply sheet obtained by laminating two first fibrous sheets) were prepared, and the contraction rates of the elastic members were compared without subjecting the respective multi-ply sheets to heating treatment. As a result, it was found that the multi-ply sheet 30 having the second fibrous sheet 3 of the present embodiment did not easily contract, and it was confirmed that the second fibrous sheet 3 hinders contraction of the elastic member 5.

Next, the absorbent body 14 is described. FIG. 6 is an outline view illustrating the absorbent body 14 provided with the surface material 15 according to the present embodiment, and FIG. 7 is a cross-sectional view along a line C-C of FIG. 6.

The absorbent body 14 provided with the surface material 15 has a gather part 21 provided at the skin surface side, and a film 24 provided at the non-skin surface side.

The gather part 21 is obtained by processing a nonwoven fabric that is a fibrous sheet, and has water repellency to ensure liquid blocking performance. To make the gather parts 21 water repellent, the gather parts 21 are coated with a water repellant such as a fluorine based-, silicone based-, or paraffin based water repellant.

The gather part 21 has a first gather 17 and an inside joined portion 18. Note that the gather part 21 and the film 24 are joined at vertical and right and left end parts (using for example, a hot-melt adhesive, heat sealing, ultrasonic bonding, and the like).

The first gather 17 prevents side leakage of urine in the Y-direction, and is formed by joining an elastic member that is the same as the elastic member 5 to the nonwoven fabric. In the present embodiment, two first gathers 17 provided with an elastic member are prepared. Note that second gathers (not illustrated) for legs may be provided outside the first gather 17.

As illustrated in FIG. 7, the first gather 17 is provided with two linear elastic bodies 5a. The linear elastic body 5a of a tip end covered by the nonwoven fabric provides a space section 17a of several millimeters (2 to 4 mm) between the linear elastic body 5a and the nonwoven fabric. By providing a space section 17a in this manner, the elastic force when the linear elastic body 5a contacts the skin can be reduced, and thereby the texture can be improved. Note that the number of linear elastic bodies 5a is not particularly limited. In addition, the elastic force thereof may be made different between the gather and the surface material 15. Furthermore, the elastic force may be differed according to gender, use for an adult, use for a child, and the like. In this case, the elastic force for a child may be set to be weaker in comparison to use for an adult.

Two first gathers 17 are provided, one each near both end parts of the surface material 15 in the Y-direction, and the inside joined portion 18 joins the gather 21 and the surface material 15. Any type of joining method may be used for joining by the inside joined portion 18, but in the present embodiment, joining is performed using a hot-melt adhesive.

Figure 6:
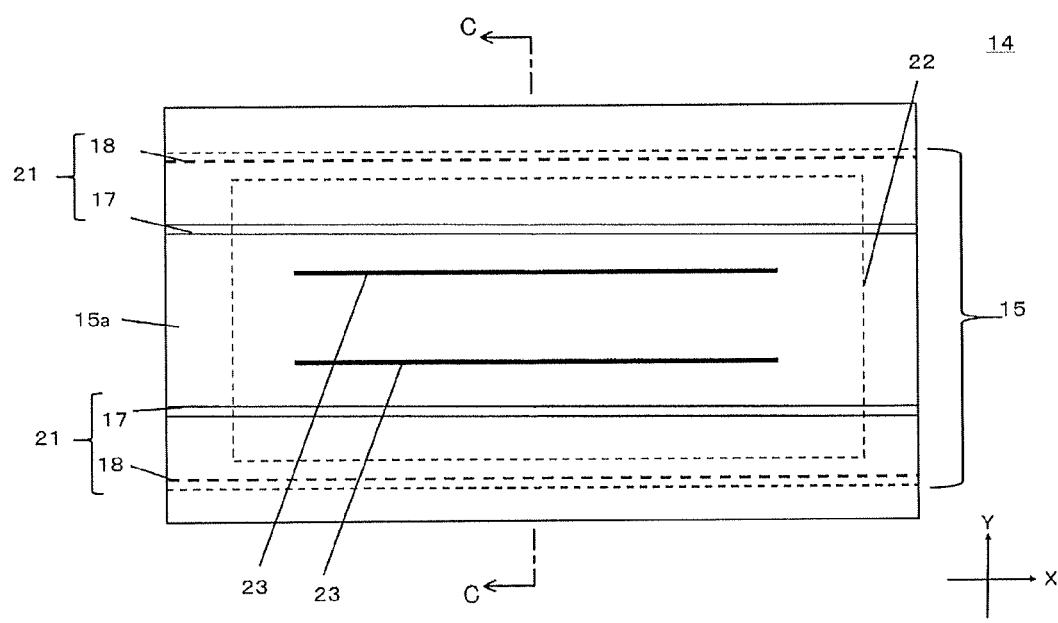
FIG. 6 is an outline view illustrating an absorbent body provided with a surface material according to one embodiment of the present invention.
Figure 7:
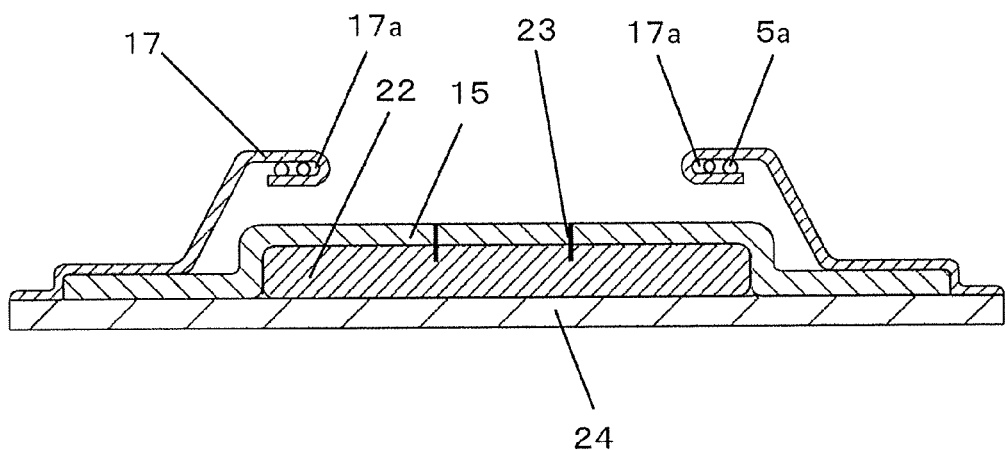
FIG. 7 is a cross-sectional view along a line C-C in FIG. 6.

Here, the gather part 21 at the positive side in the Y-direction illustrated in FIG. 6 is described. As is clear from FIG. 6, the area of the surface material 15 is larger than that of an absorbent section 22, and at the perimeter of the absorbent section 22 (at the portion where the absorbent section 22 is not present), the surface material 15 and the gather part 21 are joined without the absorbent section 22 interposed therebetween. Note that a non-joined portion 15a that is not joined is present between the surface material 15 and the gather part 21. This non-joined portion 15a is not affected by joining of the left and right end surfaces, and therefore is contracted in the X-direction by the elastic force of the elastic member 5 of the surface material 15. Note that the gather part 21 at the negative side of the Y-direction illustrated in FIG. 6 also has the same configuration as described above.

The absorbent section 22 absorbs the body fluids of a wearer, and in the present embodiment, contains pulverized pulp, and a super absorbent polymer (SAP), which is a particulate super absorbent resin.

Note that the absorbent body 14 absorbs urine, and therefore a deodorant is preferably added to the absorbent section 22. As the deodorant, activated carbon; zeolites; silica; ceramics; Oya tuff stone; charcoal polymers; carbon nanotubes; carbon nanohorns; citric acid, succinic acid, and other organic acids; and alum (potassium alum) can be used.

At the absorbent body 14, the surface material 15 and the absorbent section 22 are joined, and surface material joined portions 23 are formed along the X-direction. This allows a portion of the surface material 15 to contacts the absorbent section 22, and thus quickly guides body fluids to the absorbent section 22. Joining of the surface material 15 and the absorbent section 22 is performed through ultrasonic bonding.

The surface material joined portions 23 are provided at a prescribed interval in the Y-direction, and therefore penetration of body fluids in the Y-direction is hindered, and side leakage of body fluids can be prevented.

In FIG. 6, two surface material joined portions 23 are formed in straight line shapes, but the surface material joined portions 23 may be divided midway. The surface material joined portions 23 may also be formed by pressing the surface material 15 and the absorbent section 22 through embossing of the absorbent body 14 provided with the surface material 15.

Figure 8:
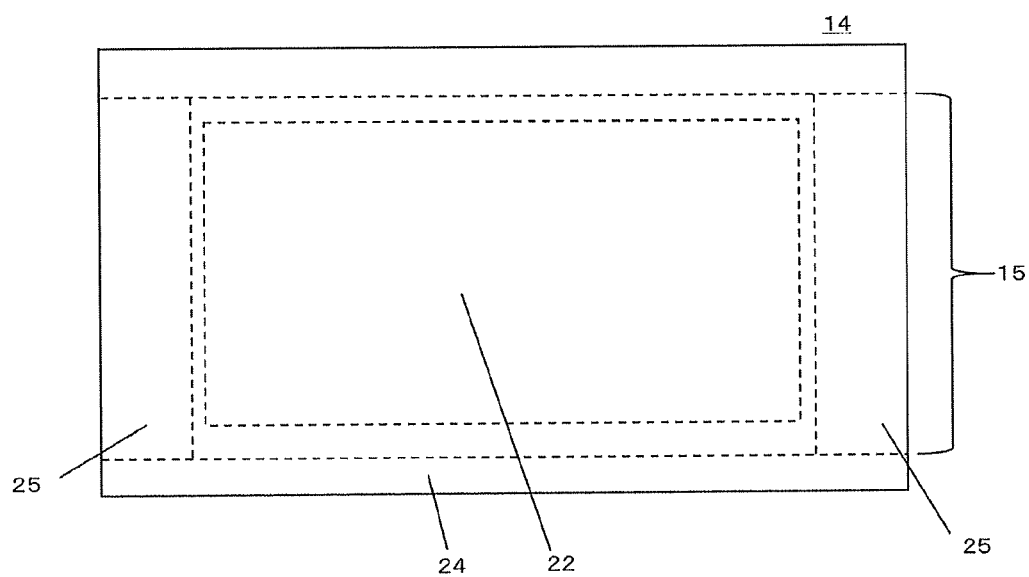
FIG. 8 is an outline view illustrating a non-skin surface side of the absorbent body according to one embodiment of the present invention.

FIG. 8 is an outline view illustrating a non-skin surface side of the absorbent body 14 according to the present embodiment. FIG. 8 illustrates the film 24, the film side shirring portions 25, and the like. The film 24 is a well-known moisture permeable film that allows permeation of vapor without allowing permeation of liquid.

The film side shirring portions 25 are formed by the elastic member 5 of the surface material 15 by releasing the stretched state of the film in the X-direction after the gather parts 21 and the film 24 have been joined.

Figure 9:
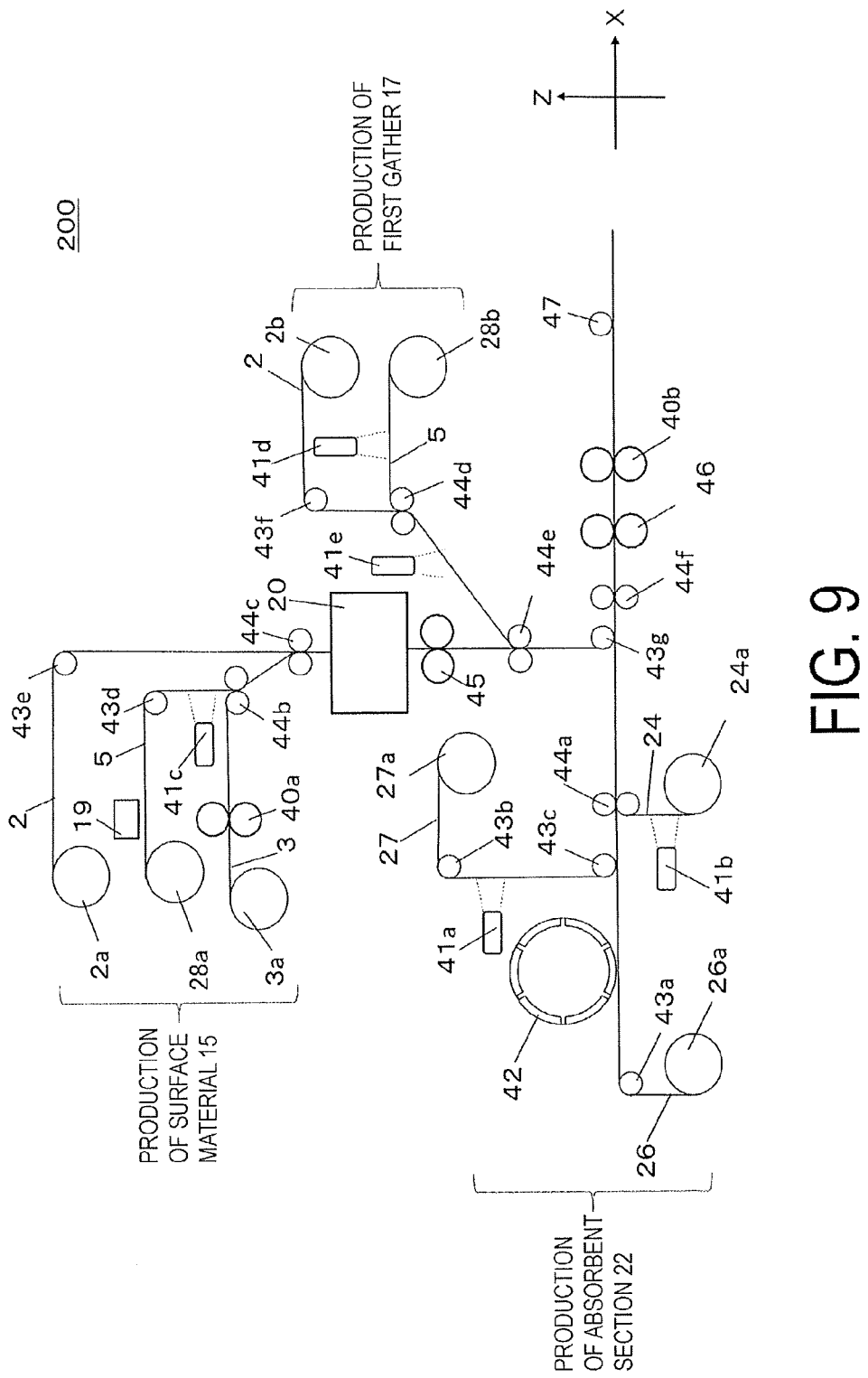
FIG. 9 is a schematic view illustrating a configuration of an absorbent body production device according to one embodiment of the present invention.
Figure 10:
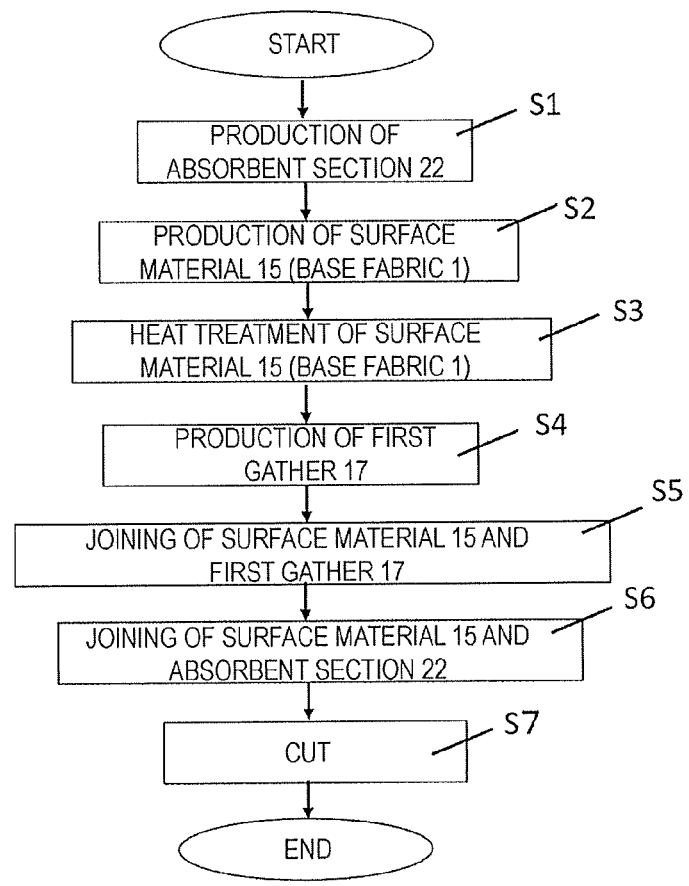
FIG. 10 is a flowchart illustrating an absorbent body production method according to one embodiment of the present invention.

Next, a device for producing the absorbent body 14 and the production method thereof are described. FIG. 9 is a schematic view illustrating a configuration of an absorbent body production device 200 according to the present embodiment, and FIG. 10 is a flowchart illustrating an absorbent body production method according to the present embodiment.

Step S1: Production of Absorbent Section 22

A lower side wrapping sheet 26 wound onto a wrapping sheet roller 26a is unwound by a conveyance roller 43a. The lower side wrapping sheet 26 may be formed from paper, a nonwoven fabric, or the like, and preferably has water repellency to cause body fluids to be absorbed by an absorbent member containing pulverized pulp and SAP, and the like. In this case, the lower side wrapping sheet 26 may be coated with a water relpellant such as a fluorine based-, a silicone based-, or a paraffin based water relpellant.

Note that with the absorbent body production device 200, a plurality of conveyance rollers 43 are used, and therefore in order to distinguish these rollers, symbols (letters) are added to facilitate the description. However, the same conveyance rollers may be used for all of the conveyance rollers, or conveyance rollers of different sizes and different rotational speeds may be used.

The lower side wrapping sheet 26 is unwound from the wrapping sheet roller 26a, and the absorbent member containing pulverized pulp and SAP is supplied from an absorbent member supply device 42.

The absorbent member supply device 42 has a rotating drum, and a plurality of recesses are formed in the outer circumferential surface of the rotating drum. The absorbent member containing pulverized pulp and SAP is supplied to the recess positioned at the top part, and the absorbent member is moved downward in association with rotation of the rotating drum while being suctioned. The absorbent member is supplied from the recess positioned at the bottom part to the surface of the lower side wrapping sheet.

An upper side wrapping sheet 27 wound onto a wrapping sheet roller 27a is unwound and conveyed by conveyance rollers 43b and 43c. The upper side wrapping sheet 27 is formed from paper, a nonwoven fabric, or the like, and preferably has water repellency to cause body fluids to be absorbed by the absorbent member. In this case, a hydrophilization treatment such as adding a hydrophilizing agent may be performed on the upper side wrapping sheet 27.

The upper side wrapping sheet 27 unwound from the wrapping sheet roller 27a is coated with an adhesive by an adhesive coating device 41a. In the present embodiment, a hot-melt adhesive is used, but another type of adhesive may be used.

The adhesive coating device 41a has a plurality of nozzles, and applies the hot-melt adhesive in a spray form onto the upper side wrapping sheet 27. In the drawing, a single adhesive coating device 41a is illustrated, but the number thereof can be set as appropriate (the same applies to other adhesive coating devices 41b to 41d).

Note that with the absorbent body production device 200, a plurality of adhesive coating devices 41 are used, and therefore in order to distinguish these rollers, symbols (letters) are added to facilitate the description. However, the same adhesive coating devices 41 may be used for all of the adhesive coating devices 41, or adhesive coating devices 41 that differ in terms of the coating amount, coating temperature, viscosity and the like may be used. Moreover, the position of the adhesive coating device 41 can be set and changed as appropriate such that the adhesive coating device 41 is disposed at an upper side with regard to a coating target, or is disposed at a lateral side.

Pulverized pulp and SAP (absorbent member) are interposed between the lower side wrapping sheet 26 and the upper side wrapping sheet 27, and the absorbent member is covered. The upper side wrapping sheet 27 may also be omitted, and the lower side wrapping sheet 26 may be used to wrap the absorbent member.

The film 24 wound onto a film roll 24a is unwound from the film roll 24a. The film 24 unwound from the film roll 24a is coated with a hot-melt adhesive from the adhesive coating device 41b.

The lower side wrapping sheet 26 and the upper side wrapping sheet 27 covering the absorbent member, and the film 24 are laminated, and are pressed and integrated by a pressing device 44a having a pair of rollers. Through this, the absorbent section 22 is produced.

Note that with the absorbent body production device 200, a plurality of pressing devices 44 are used, and therefore in order to distinguish these pressing devices, symbols (letters) are added to facilitate the description, but the same pressing device 44 may be used for all of the pressing devices 44, or pressing devices 44 of different pressing forces may be used.

Moreover, in the absorbent body production device 200, a case in which a single absorbent member supply device 42 is provided is presented, but two absorbent member supply devices 42 may be provided to laminate two layers of absorbent members. In this case, the size of each layer may be the same, or the size of the layer positioned at the skin surface side (skin surface side layer) when the absorbent body 14 is worn may be smaller than the size of the layer of the non-skin surface side.

In the case of the latter, when the absorbent section 22 is configured for male use, the center of the skin surface side layer may be shifted from the center of the non-skin surface side layer so as to be aligned with the position of the urethral opening when the absorbent body 14 is worn. On the other hand, when the absorbent section 22 is configured for female use, the center of the skin surface side layer may overlap the center of the non-skin surface side layer or may be shifted from the center of the non-skin surface side layer so as to be aligned with the position of the urethral opening when the absorbent body 14 is worn.

Step S2: Production of Surface Material 15 (Base Fabric 1)

The second fibrous sheet 3 wound onto a fibrous sheet roll 3a is unwound from the fibrous sheet roll 3a, and is embossed by a pair of embossing rollers 40a. Embossing has an action of making the second fibrous sheet 3 flexible, and therefore this treatment is referred to as "mechanical flexibility imparting treatment". Note that with the absorbent body production device 200, a plurality of embossing rollers 40 are used, and therefore in order to distinguish these rollers, symbols (letters) are added to facilitate the description. The same embossing rollers 40 may be used for all of the embossing rollers 40, or embossing rollers 40 of different embossing patterns, sizes, materials, and the like may be used.

The elastic member 5 wound onto an elastic roll 28a is unwound from the elastic roll 28a, and is heated by a first heating device 19.

The first heating device 19 is a non-contact heating device which supplies air of a temperature of 30° C. to 80° C., for example. For example, in a case where the air temperature in a plant in which the absorbent body production device 200 is installed is 15° C. or lower, the elastic member 5 does not easily expand and contract, and therefore the first heating device 19 is used to prevent this. In a case where polyurethane is used as the elastic member 5, the heat resistance of polyurethane is around 80° C., and therefore the first heating device 19 may be set to supply air at a temperature of 80° C. or lower (preferably 40° C. to 60° C.).

Note that the first heating device 19 is not particularly limited, and electromagnetic waves or infrared rays may be used. Heating of the elastic member 5 by this first heating device 19 is a part of the heating treatment of the surface material 15 in the below-described step S3. Furthermore, when the air temperature within the plant is controlled, for example, to a temperature of 20° C. or higher, the first heating device 19 may be omitted.

The hot-melt adhesive (adhesive 7) is applied by the adhesive coating device 41c onto the elastic member 5 heated by the first heating device 19. To simplify the drawing, only one elastic roll 28a is illustrated, but a plurality of elastic rolls 28a may be arranged according to the number of elastic members 5 that are to be used. Moreover, the elastic member 5 for the surface material 15, and the elastic member 5 for the first gather 17 may be of the same elastic force, or may be of different elastic forces. In the case of the latter, the elastic force of the elastic member 5 for the surface material 15 may be set to be stronger than the elastic force of the elastic member 5 for the first gather 17.

The embossed second fiber sheet 3 and the elastic member 5 coated with the hot-melt adhesive are pressed by the pressing device 44b, which has a pair of pressing rollers, and through this, the second fibrous sheet 3 and the elastic member 5 are joined (adhered).

The first fibrous sheet 2 wound onto a fibrous sheet roll 2a is unwound by the conveyance roller 43e. This first fibrous sheet 2 is subjected in advance to a hydrophilization treatment.

The second fibrous sheet 3 to which the elastic member 5 has been joined and the first fibrous sheet 2 are pressed by the pressing device 44c, and are joined (adhered) by the hot-melt adhesive (adhesive 7) applied onto the peripheral surface of the elastic member 5. Through this, the surface material 15 is produced.

Note that the surface material 15 is not limited to being produced in-line with the absorbent body production device 200, and the surface material 15 may be produced in advance, and the pre-produced surface material 15 may be attached to a roll member, which is not illustrated, and introduced to the absorbent body production device 200.

Step S3: Surface Material 15 (Base Fabric 1) Heating Treatment

The surface material 15 is heated by the second heating device 20. Note that in a case where heating is performed by the above-described first heating device 19, the heating thereof is included in the step 3 of heating treatment of the surface material 15. The second heating device 20 is not particularly limited, and any of aeration, electromagnetic waves or infrared rays may be used, but non-contact heating is preferable.

The second heating device 20 heats the surface material 15 at a temperature setting of around 40° C. to 150° C. for several seconds to several tens of seconds, and may heat at a heating value that is the same or greater than that of the first heating device 19. Furthermore, the second heating device 20 may heat one side of the surface material 15 (for example, the first fibrous sheet 2 side), or may heat both sides of the surface material 15.

The second heating device 20 softens the cured hot-melt adhesive through heating, and can eliminate the residual strain of the surface material 15.

One of the thermal characteristics of the hot-melt adhesive is the boundary temperature range (hereinafter, referred to as "softening point") at which the hot-melt adhesive changes from a solid to a liquid. The softening point differs depending on the type of hot-melt adhesive, but is around approximately 85° C. to 155° C. In the present embodiment, a hot-melt adhesive having a softening point of approximately 85° C. to around 120° C. (preferably, approximately 85° C. to around 100° C.) is used, and the hot-melt adhesive is heated by the second heating device 20 until just before softening (for example, to a temperature that is around 1° C. to 20° C. lower than the softening point). This is because heating the hot-melt adhesive to the softening point by the second heating device 20 impacts the joining (adherence) of the first fibrous sheet 2 and the second fibrous sheet 3 with the hot-melt adhesive interposed therebetween.

As described above, the heat resistance of polyurethane is around 80° C., and therefore use of a hot-melt adhesive having a softening point close to the heat resistance temperature of the elastic member 5, or a hot-melt adhesive having a softening point up to 20° C. higher than the heat resistance temperature of the elastic member 5 is preferable. This is because, as described above, the second heating device 20 is set to a heating temperature that is around 1° C. to 20° C. lower than the softening point of the hot-melt adhesive.

Note that the second heating device 20 may be set to a temperature that exceeds the heat resistance temperature of the elastic member 5, but as described above, the hot-melt adhesive is applied to the peripheral surface of the elastic member 5, and the elastic member 5 is interposed between the first fibrous sheet 2 and the second fibrous sheet 3, and the heating time is controlled, and thereby the elastic member 5 itself is not substantially exposed to a temperature that exceeds the heating temperature.

The surface material 15 heated by the second heating device 20 is heated by a third heating device 45. The third heating device 45 is a contact-type heating device having a pair of rollers, and both rollers of the pair of rollers may be heating rollers to heat both sides of the surface material 15, or only one of the rollers (for example, the roller on the first fibrous sheet 2 side) may be a heating roller. Furthermore, the number of pairs of rollers and the arrangement can be optionally set.

Heating by the third heating device 45 may be performed at the same heating temperature as that of the first heating device 19, or at a heating value higher than the heating temperature of the first heating device 19, and the heating temperature thereof may be set to about the same temperature as that of the second heating device 20. Note that in a case where the residual strain of the surface material 15 can be eliminated by the second heating device 20, the third heating device 45 may be omitted.

Through heating by the second heating device 20 and the third heating device 45, the hot-melt adhesive can be temporarily softened, and the residual strain of the surface material 15 can be eliminated. The absorbent body production device 200 may be configured such that the contraction rate of the sample of the surface material 15 is periodically (for example, before starting production with the absorbent body production device 200 each day) measured, and heating conditions such as the heating temperature and heating time by the second heating device 20 and the third heating device 45 are set.

For cases in which the second heating device 20 and the third heating device 45 heat the first fibrous sheet 2 that will be positioned at the skin surface side, nap formation on the surface of the first fibrous sheet 2 can be suppressed, and the texture of the surface material 15 can be improved.

Step S4: Production of First Gather 17

The water repellent nonwoven fabric wound on a fibrous sheet roll 2b is unwound by a conveyance roller 43f. Two water repellent nonwoven fabrics are wound with an interval therebetween onto this fibrous sheet roll 2b. This is done to produce the two first gathers 17 illustrated in FIG. 6. By winding two water repellent nonwoven fabrics onto a single fibrous sheet roll 2b, the absorbent body production device 200 can be made compact without the conveyance timing of the two water repellent nonwoven fabrics being shifted. Note that the water repellent nonwoven fabric is subjected in advance to a water repellency treatment.

The elastic member 5 wound onto an elastic roll 28b is unwound from the elastic roll 28b, and is coated with a hot-melt adhesive by the adhesive coating device 41d. The water repellent nonwoven fabric and the elastic member 5 coated with the hot-melt adhesive are pressed and joined by a pressing device 44d. Through this, two first gathers 17 can be produced.

Step S5: Joining of Surface Material 15 and First Gather 17

A hot-melt adhesive is applied onto the two first gathers 17 by the adhesive coating device 41e.

The two first gathers 17 and the surface material 15 are pressed by a pressing device 44e, and the two first gathers 17 are joined to the surface material 15.

Note that the heating treatment of step S3 may be performed after the two first gathers 17 are joined to the surface material 15. Through this, the residual strain in both the surface material 15 and the first gather 17 can be reduced all at once.

Step S6: Joining of Surface Material 15 and Absorbent Section 22

The surface material 15 for which the two first gathers 17 are joined, and the absorbent section 22 are pressed by a pressing device 44f, and the absorbent section 22 and the surface material 15 are joined. Next, the surface material 15 and the absorbent section 22 are ultrasonically bonded by an ultrasonic bonding device 46, and thereby two surface material joined portions 23 are formed. Through this, a portion of the surface material 15 and a portion of the absorbent section 22 are joined, and therefore body fluids are quickly transmitted from the surface material 15 to the absorbent section 22, and discomfort of the user can be reduced. Note that in place of the surface material joined portion 23 or in combined use therewith, the entire surface of the surface material 15 may be embossed by a pair of embossing rollers 40b. In addition, rather than embossing rollers. flat rollers may be used, and in this case, the rollers may be heating rollers. Through this, the surface material 15 and the absorbent section 22 easily contact each other, and body fluids can be quickly transmitted to the absorbent section 22.

Step S7: Cutting

The absorbent body 14 is cut by a cutting device 47, into individual absorbent bodies 14. The residual strain of the surface material 15 has been reduced, and therefore even when this cutting is performed, the absorbent body 14 does not deform.

Note that after this cutting step, a step of folding the absorbent body 14, a step of packaging in a box, and the like may be added. Moreover, a hydrophilic nonwoven fabric may be added as a sublayer to the absorbent body 14.

The flowchart of FIG. 10 is merely one example, and the order of each step may be switched, as appropriate, according to the production conditions.

In this way, according to the present embodiment, the elastic member 5, which has hot-melt adhesive coated onto the peripheral surface and is in a stretched state, is sandwiched between the first fibrous sheet 2 and the second fibrous sheet 3 and laminated to form the surface material 15, and the surface material 15 is heated at a temperature which is at or below the softening point of the hot-melt adhesive, and at or above a prescribed temperature with respect to the heat resistance temperature of the elastic member 5. Through this, the residual strain of the surface material 15 can be reduced, and deformation of the absorbent body 14 in which the surface material 15 is used can be prevented.

Other Embodiment

In another embodiment of the present invention, in contrast to the multi-ply sheet 30 of the first embodiment, a case is described in which a third fibrous sheet that is the same as the first fibrous sheet 2 is added to the non-skin surface side of the second fibrous sheet 3 to form a multi-ply sheet having a three-layer configuration, and is used as an external sheet 11 of a disposable underwear 10.

When the base fabric of a three-layer configuration is used as the external sheet 11 of the disposable underwear 10, at least one of the first fibrous sheet 2 and the third fibrous sheet is desirably a water repellent sheet. As the water repellent nonwoven fabric, a three-layer spunbond nonwoven fabric can be used, and a water repellency treatment which applies a coating of a fluorine based-, silicone based-, paraffin based-, or alkylchromic chloride water repellant is preferably performed. Note that the basis weight of the water repellent nonwoven fabric is, as one example, preferably 10 to 50 g/m², and from the viewpoint of production costs, and is more preferably 10 to 20 g/m², but the basis weight is not limited thereto.

Figure 11:
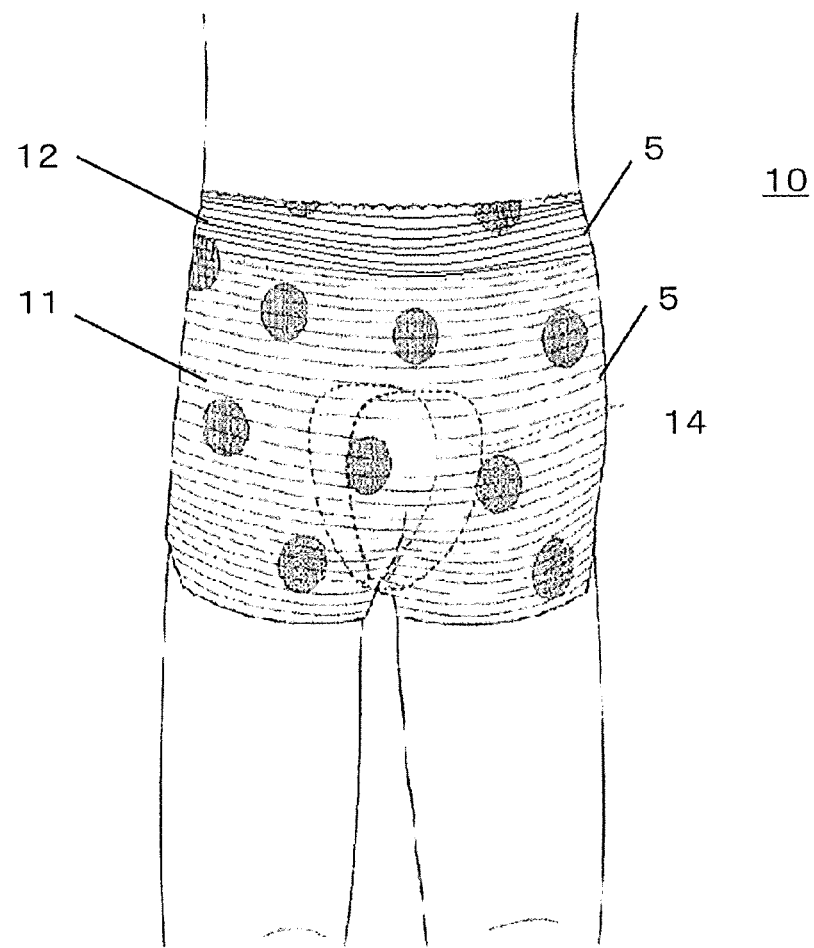
FIG. 11 is a drawing illustrating a condition in which an absorbent body is attached to a disposable underwear according to another embodiment of the present invention, and worn.

FIG. 11 is a drawing illustrating a condition in which the absorbent body 14 is attached to the disposable underwear 10 according to the other embodiment of the present invention, and worn. The disposable underwear 10 is described below with reference to FIG. 11. Note that while not illustrated in FIG. 11, adhesive tape, for example, is provided at the attachment surface of the non-skin surface side of the absorbent body 14 (in two places for example) so that the absorbent body 14 can be attached to and removed from the disposable underwear 10.

The disposable underwear 10 has the external sheet 11 and a torso attachment part 12. The torso attachment part 12 is formed by folding a portion of the external sheet 11, and is positioned around the waist of the user when worn.

In the present embodiment, the external sheet 11 is obtained by laminating, in order from the skin surface side of the user, the first fibrous sheet 2, the elastic member 5, and the second fibrous sheet 3, and is further configured with the third fibrous sheet, which is the same as the first fibrous sheet 2, added to the non-skin surface side of the second fibrous sheet 3. Water repellent nonwoven fabrics are used for the first fibrous sheet 2 and the third fibrous sheet, and the sheets thereof are coated with a water relpellant such as a fluorine based-, silicone based-, or paraffin based water relpellant.

As described above, the torso attachment part 12 is formed by folding the external sheet 11. Therefore, compared to other portions, the elastic members 5 (linear elastic bodies 5a) are densely arranged, and the elastic force acting around the waist of the user becomes stronger than at other portions. Therefore, when the disposable underwear 10 is worn, the disposable underwear 10 is not easily shifted downward. Note that the torso attachment part 12 may also be formed without folding the external sheet 11.

The elastic members 5 are provided such that they can expand and contract in the lateral direction of FIG. 11, but may also be arranged so as to expand and contract in the vertical direction in the drawing.

Furthermore, as is clear from FIG. 11, a pattern is formed on the disposable underwear 10. This pattern is printed onto the second fibrous sheet 3, and can be printed, as appropriate, using gravure printing, flexographic printing or other such printing method.

The disposable underwear 10 can withstand washing multiple times, and therefore can be used for a certain period of time, and is economical. In addition, the disposable underwear 10 can be used regardless of age, gender, or body shape (for children, for men, for women, and the like), and can be adapted for use on pets and other animals.

Note that a base fabric having the first fibrous sheet 2, the elastic member 5, the second fibrous sheet 3, and the third fibrous sheet may also be used as an external body of a diaper rather than for the disposable underwear 10.

The disposable underwear 10 also includes the elastic member 5 to which the hot-melt adhesive is applied, and the second fibrous sheet 3. Thus, the external sheet 11 is desirably produced by performing a heating treatment using the first heating device 19, the second heating device 20, and the third heating device 45 as described with the production of the surface material 15.

The device for producing the external sheet 11 can be realized by adding, to the production device for the surface material 15, a roll member for installing the third fibrous sheet, conveyance rollers, and the like. In this case, a production device for producing the first gather 17 and the absorbent section 22 is not necessary, and a device for producing the disposable underwear 10 can be achieved by adding devices such as a hole forming device for forming hole parts through which both legs can be inserted to put on the disposable underwear 10. Note that the production device can be tailored to the production of the disposable underwear 10 and varied including, for example, omitting the first heating device 19, or omitting the third heating device 45.

The present embodiment was described above, but the present invention is not limited thereto, and of course various modifications and appropriate combinations are possible. For example, the layout of the linear elastic bodies 5a is not limited to linear extension in the X-direction, and the linear elastic bodies 5a may be intermittent linear elastic bodies 5a; curved linear elastic bodies 5a that are curved may be arranged in parallel, and curved linear elastic bodies 5a having a wave form may be aligned in an irregular manner and arranged. With respect to an arrangement of a large number of linear elastic bodies 5a, the linear elastic bodies 5a may be combined with each linear elastic body 5a having a different stretching ratio. The elastic member 5 is not limited to a linear form, and a sheet-shaped elastic body provided with a large number of holes or notches to ensure a predetermined air permeability can be also used.

All of the details contained in U.S. Provisional Application 62/308,974 filed on Mar. 16, 2016 are incorporated by reference in the present application.

REFERENCE SIGNS LIST

1 Base fabric
2 First fibrous sheet
3 Second fibrous sheet
5 Elastic member
6 Concave-convex row
10 Disposable underwear
14 Absorbent body
15 Surface material
20 Second heating device
24 Film
40 Embossing roller
41 Adhesive coating device
42 Absorbent member supply device
44 Pressing device
45 Third heating device
46 Cutting device
200 Absorbent body production device

The invention claimed is:

1. A method for producing a multi-ply sheet, comprising:
   forming a multi-ply sheet by joining with an adhesive a first fibrous sheet and a second fibrous sheet with an elastic member in a stretched state interposed therebetween; and
   heat-treating the multi-ply sheet at a temperature in accordance with thermal characteristics of the adhesive while the elastic member is in the stretched state,
   wherein the temperature of the heat treatment is 1° C. to 20° C. lower than a softening point of the adhesive.

2. The multi ply sheet production method according to claim 1, wherein the temperature of the heat treatment is in accordance with heat resistance of the elastic member.

3. The method according to claim 1, wherein the softening point of the adhesive is in accordance with heat resistance of the elastic member.

4. The method according to claim 1, wherein
   the first fibrous sheet is a nonwoven fabric; and
   the heat treatment is performed such that nap of the nonwoven fabric is treated.

\* \* \* \* \*